United States Patent [19]

Houlihan

[11] 4,140,859

[45] Feb. 20, 1979

[54] DILITHIATED 2-(O-TOLYL)-2-IMIDAZOLINES

[75] Inventor: William J. Houlihan, Mountain Lakes, N.J.

[73] Assignee: Sandoz, Inc., E. Hanover, N.J.

[21] Appl. No.: 896,155

[22] Filed: Apr. 13, 1978

Related U.S. Application Data

[60] Division of Ser. No. 520,537, Nov. 4, 1974, Pat. No. 4,101,553, which is a continuation-in-part of Ser. No. 429,526, Jan. 2, 1974, abandoned.

[51] Int. Cl.$^2$ .................. C07D 233/06; C07D 233/20
[52] U.S. Cl. .................................................. 548/347
[58] Field of Search ........................................ 548/347

[56] References Cited

PUBLICATIONS

Hill et al., J. Amer. Chem. Soc. 1954, vol. 76, pp. 922–923.
Oxley et al., J. Chem. Soc. (London) 1947, pp. 497–505.
Sawa et al., Chem. Abst. 1967, vol. 66, No. 95042g.

*Primary Examiner*—Natalie Trousof
*Attorney, Agent, or Firm*—Gerald D. Sharkin; Robert S. Honor

[57] ABSTRACT

Imidazo[2,1-a]isoquinolines useful as anorexics and antidepressants are prepared from a dilithium derivative of a 2-(o-tolyl)-2-imidazoline.

2 Claims, No Drawings

DILITHIATED 2-(O-TOLYL)-2-IMIDAZOLINES

This is a division of application Ser. No. 520,537 filed Nov. 4, 1974 now U.S. Pat. No. 4,101,553, which in turn is a continuation-in-part of Ser. No. 429,526, filed Jan. 2, 1974, now abandoned.

This invention relates to imidazo[2,1-a]isoquinolines of the formula (I)

where
$R_o$ represents H or halo of atomic weight 19–36,
each of
R, $R_1$ and $R_2$ represents, independently, H, halo having an atomic weight of 19–36, methyl, methoxy, trifluoromethyl, or
R and $R_1$ or $R_1$ and $R_2$ taken together represent methylenedioxy, $R_2$ and $R_o$ and R and $R_o$ respectively then being H, and
$R_3$ represents H, halo having an atomic weight of 19–36, or methyl,
provided that
(1) when R or $R_2$ is trifluoromethyl, $R_1$ is H or said halo, and
(2) no more than two of R, $R_1$, $R_2$ and $R_o$ represent other than H.

The invention also concerns a process for producing said compounds (I), acid addition salts thereof and intermediates therefor.

The compounds of formula (I) may also be represented by the tautomeric form (Ia):

(Ia)

where R, $R_1$, $R_2$, $R_3$ and $R_o$ are as above defined. To simplify this disclosure, only the compounds of formula (I) are to be discussed but both tautomeric forms are included in the context of this invention.

The compounds (I) may be prepared by treating a dilithiated derivative of a 2-(o-tolyl)-2-imidazoline (II)

with a compound of the formula (III)

where
R, $R_1$, $R_2$, $R_3$ and $R_o$ are as earlier defined, and
X represents halo having an atomic weight of about 35–80, or $OR_4$ where $R_4$ represents straight chain alkyl of 1–4 carbon atoms, such as methyl, ethyl, and the like,
and hydrolyzing the resulting adduct.

This process is conducted by treating a compound (II) with a compound (III) in inert atmosphere, such as nitrogen gas, and inert solvent such as a hydrocarbon, for example, hexane or heptane, or an ether, e.g., diethyl ether or tetrahydrofuran at a temperature of about $-30°$ to $+50°$ C., preferably at about $-20°$ to $0°$ C., for about 0.5 to about 48 hours. Methyl and ethyl are preferred groups within the definition of $R_4$. The hydrolysis may be performed in conventional manner using e.g., water, dilute mineral acid, ammonium chloride solution and the like. Compounds (I) may be recovered by conventional techniques, e.g., filtration and concentration.

The particular solvent and time of the reaction are not critical in obtaining the compounds (I).

The dilithio derivative represented by compound (II) is obtained by treating a compound of the formula (IV)

where $R_3$ is as above defined with a compound of formula $R_5Li$ (V)

where $R_5$ represents alkyl of 1–4 carbons such as methyl, ethyl, isopropyl, and the like, under reaction conditions essentially similar to those set out above for obtaining compounds (I) from compounds (II) and (III), but at a temperature of from about 25°–75° C., preferably about 35° C.

Some of the compounds of formulas (III) and (IV) are known and may be prepared according to methods disclosed in the literature. Those compounds of formulas (III) and (IV) not specifically disclosed in the literature may be prepared using analogous methods and known compounds.

The compounds of formula (I) are useful because they possess pharmacological activity in animals. In particular, they possess appetite depressant activity as indicated by their activity in rats given 25 mg/kg of the active agent and tested by use of the free-feeding method described by Randall, et al. (J. Pharmacol. Exp. Ther., 129, 163, 1960) whereby 16 groups of six male Wistar rats are deprived of food for 18 hours but receive water ad libitum. Consumption of ground food is then measured over a four hour period following oral administration of the agent tested. Accordingly, these compounds may be used as anorexigenic agents. The compounds of this invention also possess central nervous system stimulant activity and can be used as anti-depressants as indicated by their activity in mouse given 0.7–25.6 mg/kg of active compound and tested according to the method of Spencer, P. S. J., Antagonism of Hypothermia in the Mouse by Anti-depressants, in Anti-depressant Drugs, p. 194–204, Eds. S. Garattini and M. N. G. Dukes, Excerpta Medica Foundation, 1967. In this method, reserpine (5.0 mg/kg i.p.) is administered to groups of 5 mice. After one hour, selected doses of the test compound are administered i.p. Rectal temperatures are taken 2, 1 and 0 hours pre-reserpine and 1, 3 and 5 hours post-reserpine.

When the compounds (I) are employed for the above utilities, they may be combined with one or more pharmaceutically acceptable carriers or adjuvants and may be administered orally in such forms as tablets, capsules, elixirs, suspensions and the like, parenterally in the form of an injectable solution or suspension or in special forms such as suppositories and the like. Depending upon the compound employed and the mode of administration, the exact dosage utilized may vary. A representative formulation suitable for oral administration 2 to 4 times per day for the treatment of overweight or depression is a capsule prepared by standard encapsulating techniques which contains 50 mg. of 4-(p-fluorophenyl)-2,3,5,6-tetrahydro-imidazo[2,1-a]isoquinolin-5-ol, and 200 mg. of an inert solid diluent such as starch, lactose or kaolin.

In general, satisfactory results are obtained for each of the above-mentioned uses when the compounds are administered at a daily dosage of from about 0.05 milligrams to about 25 milligrams per kilogram of animal body weight, preferably given in divided doses 2 to 4 times a day, or in sustained release form. For most large mammals the daily dosage is generally in the range of from about 2.5 milligrams to about 75 milligrams and dosage forms suitable for internal administration comprise from about 0.7 milligrams to about 40 milligrams of the compound admixed with a solid or liquid pharmaceutical carrier or diluent.

Furthermore, the compounds of formula (I) may be similarly administered in the form of their non-toxic pharmaceutically acceptable acid addition salts. Such salts possess the same order of activity as the free base are readily prepared by reacting the base with an appropriate acid, and, accordingly, are included within the scope of the invention. Representative of such salts are the mineral acid salts, such as the hydrochloride, hydrobromide, sulfate, phosphate and the like and the organic acid salts, such as the succinate, benzoate, acetate, maleate and the like. These salts may exist in either of the tautomeric forms (I) or (Ia) and in the specification and claims it will be understood that both forms are intended to be embraced by the reference to salt forms.

EXAMPLE 1

Into a flask maintained under nitrogen and equipped with a stirrer, condenser and dropping funnel is charged 6.26 g (0.04 mole) of 2-(o-tolyl-2(1H)-imidazoline and 100 ml. of dry tetrahydrofuran. The solution is stirred, treated with 84 ml of 1.6 M n-butyl lithium (0.13 mole) in hexane and maintained at 35° C. for ca. 5 hours. The mixture is treated with 20.7 g (0.16 mole) of ethyl p-fluorobenzoate in 50 ml of dry tetrahydrofuran and then maintained at 50° C. for ca 5 hours. The reaction is then cooled in an icebath and treated with 22.8 ml of saturated ammonium chloride. The tetrahydrofuran layer is separated in a separatory funnel, dried with magnesium sulfate, filtered and then concentrated in vacuo. The residue is dissolved in a hot methylene chloride-ethanol (1:1) mixture to give on cooling 5-(p-fluorophenyl)-2,3,5,6-tetrahydro-imidazo[2,1-a]isoquinolin-5ol, m.p. 189°–190° C. This compound is a preferred embodiment of this invention.

The product of this example is useful in treating depression or in suppressing appetite at a dosage of 2 mgs. in capsules administered 2-4 times per day.

When the above process is carried out and in place of 2-(o-tolyl)-2-imidazoline there is used an equivalent amount of
(a) 2-(4-chloro-2-tolyl)-2-imidazoline or
(b) 2-(2,4-xylyl)-2-imidazoline, there is obtained
(a) 8-chloro-4-(p-fluorophenyl)-2,3,5,6-tetrahydroimidazo[2,1-a]isoquinolin-5-ol, or
(b) 5-(p-fluorophenyl)-8-methyl-2,3,5,6-tetrahydroimidazo[2,1-a]isoquinolin-5-ol, respectively.

When the above detailed process is carried out and in place of ethyl-p-fluorobenzoate there is used an equivalent amount of
(c) methyl-p-chlorobenzoate,
(d) m-fluorobenzoylchloride,
(e) ethyl-m-trifluoromethylbenzoate,
(f) ethylbenzoate,
(g) ethyl-p-toluate,
(h) ethyl-p-methoxybenzoate,
(i) ethyl-3,4-methylenedioxybenzoate,
(j) ethyl-3,4-dichlorobenzoate,
(k) ethyl-o-chlorobenzoate, or
(l) ethyl-2,4-dichlorobenzoate, there is obtained
(c) 5-(p-chlorophenyl)-2,3,5,6-tetrahydroimidazo[2,1-a]isoquinolin-5-ol,
(d) 5-(m-fluorophenyl)-2,3,5,6-tetrahydroimidazo[2,1-a]isoquinolin-5-ol,
(e) 5-(p-trifluoromethylphenyl)-2,3,5,6-tetrahydroimidazo[2,1-a]isoquinoline-5-ol,
(f) 5-phenyl-2,3,5,6-tetrahydroimidazo[2,1-a]isoquinolin-5-ol,
(g) 5-(p-tolyl)-2,3,5,6-tetrahydroimidazo[2,1-a]isoquinolin-5-ol,
(h) 5-(p-methoxyphenyl)-2,3,5,6-tetrahydroimidazo[2,1-a]isoquinolin-5-ol,
(i) 5-(3,4-methylenedioxyphenyl)-2,3,5,6-tetrahydroimidazo[2,1-a]isoquinolin-5-ol,
(j) 5-(3,4-dichlorophenyl)-2,3,5,6-tetrahydroimidazo[2,1-a]isoquinolin-5-ol,
(k) 5-(2-chlorophenyl)-2,3,5,6-tetrahydroimidazo[2,1-a]isoquinolin-5-ol, or
(l) 5-(2,4-dichlorophenyl)-2,3,5,6-tetrahydroimidazo[2,1-a]isoquinolin-5-ol respectively.

EXAMPLE 2

5-(p-Chlorophenyl)-2,3,5,6-tetrahydroimidazo[2,1-a]isoquinolin-5-ol

To a flask equipped with a stirrer, condenser, thermometer and dropping funnel is charged 8.0 g. (0.05 mole) of 2-(o-tolyl)-2(1H)-imidazoline and 200 ml. of anhydrous tetrahydrofuran. The reaction is blanketed with nitrogen and dropwise at room temperature is added a solution of 105 ml. (0.15 mole n-butyllithium) of 1.6 molar n-butyllithium in hexane. The mixture is then stirred and heated at 35° C. for ca 5 hours. The heating is stopped and the flask is immersed in a dry-ice acetone bath. The flask is cooled until the internal temperature is about −20° C., and then treated dropwise with a solution of 17.5 g. (0.10 mole) of methyl-p-chlorobenzoate and 100 ml. anhydrous tetrahydrofuran at such a rate that the internal temperature does not exceed −20° C. After the addition is complete, the mixture is maintained at ca −20° C. for 3 hours. The dry-ice bath is removed and at ca 0° C. the reaction mixture is treated dropwise with 30 ml. of saturated ammonium chloride solution while maintaining the temperature below 20° C. The reaction mixture is allowed to stand overnight at room temperature and then evaporated in vacuo. The pasty residue is treated with ca 200 ml. of methylene chloride and then 100 ml. of water. The organic layer is separated, washed with water, dried with anhydrous magnesium sulfate, filtered and concentrated in vacuo to ca 70 ml. total volume. After ca 1 hour the resultant solid is filtered to give a solid, m.p. 175°–178° C. dec. The solid is dissolved in a minimum of hot 95% ethanol and then concentrated to ca 95 ml. volume. On standing at room temperature there is obtained 5-(p-chlorophenyl)-2,3,5,6-tetrahydroimidazo[2,1-a]isoquinolin-5-ol, m.p. 198°–200° C. dec.; Rf 0.30 (CHCl$_3$/CH$_3$OH, 90:10); Analysis Calculated for C$_{17}$H$_{15}$ClN$_2$O:: C, 68.3; H, 5.1; N, 9.4. Found: C, 68.2; H, 5.4; N, 9.3.

I claim:
1. A compound of the formula

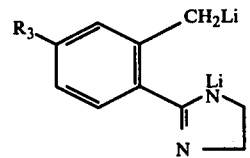

where R$_3$ represents H, halo having an atomic weight of 19–36, or methyl.

2. A compound according to claim 1 which is the dilithium salt of 2-(o-tolyl)-2-imidazoline.

* * * * *